United States Patent
Hada et al.

(10) Patent No.: US 6,767,622 B2
(45) Date of Patent: Jul. 27, 2004

(54) POROUS POLYOLEFIN FILM, PROCESS FOR PRODUCING SAME, AND USE THEREOF

(75) Inventors: Kazuyuki Hada, Tokuyama (JP); Yoshinori Takahashi, Tokuyama (JP)

(73) Assignee: Tokuyama Corporation, Tokuyama (JP)

(*) Notice: Subject to any disclaimer, the term of this patent is extended or adjusted under 35 U.S.C. 154(b) by 345 days.

(21) Appl. No.: 09/926,006

(22) PCT Filed: Dec. 13, 2000

(86) PCT No.: PCT/JP00/08794
§ 371 (c)(1),
(2), (4) Date: Oct. 31, 2001

(87) PCT Pub. No.: WO01/44353
PCT Pub. Date: Jun. 21, 2001

(65) Prior Publication Data
US 2003/0100650 A1 May 29, 2003

(30) Foreign Application Priority Data
Dec. 14, 1999 (JP) .............................. 11-355133
Jul. 11, 2000 (JP) ........................................ 2000-209325

(51) Int. Cl.$^7$ ................................................. B32B 3/00
(52) U.S. Cl. ................................ 428/315.9; 428/307.3; 428/312.2; 428/319.9; 264/288.8
(58) Field of Search ......................... 428/307.3, 311.1, 428/312.2, 315.9, 319.9; 264/288.8

(56) References Cited

U.S. PATENT DOCUMENTS

| 4,626,252 A | * 12/1986 | Nishizawa et al. |
| 5,853,638 A | * 12/1998 | Han |
| 6,140,551 A | * 10/2000 | Niemeyer et al. |

FOREIGN PATENT DOCUMENTS

| JP | 64-54042 | * 3/1989 |
| JP | 8-245818 | * 9/1996 |

* cited by examiner

Primary Examiner—Tae H. Yoon
(74) Attorney, Agent, or Firm—Westerman, Hattori, Daniels & Adrian, LLP

(57) ABSTRACT

The present invention provides a porous polyolefin film abounding in air permeability and moisture permeability and having extremely high degree of light transmission and tear strength, a process for producing same and intended use thereof. This porous polyolefin film is produced, for example, by stretching an unstretched polyolefin film having a resin composition of 100 parts by weight of polyolefin, 50–150 parts by weight of an inorganic filler having a 50% median diameter of at least 2 μm but less than 7 μm measured according to the light-scattering method, and 2–20 parts by weight of a wax of polyolefin series in at least uniaxial direction at an area magnification of 1.1–1.5 times, and possesses physical properties of a water vapor transmission rate of at least 1000 g/m$^2$·24 hrs., a light transmission of at least 65%, and a tear strength of at least 0.6 N.

11 Claims, No Drawings

POROUS POLYOLEFIN FILM, PROCESS FOR PRODUCING SAME, AND USE THEREOF

TECHNICAL FIELD

The present invention relates to a novel porous polyolefin film and to a process for producing same. More particularly, the present invention relates to a porous polyolefin film suitable for use in various medical or sanitary supplies, in particular, such as back-sheets for disposable diapers, which is excellent in vapor-permeability and liquid-imparmeability, good see-through property by virtue of light transmission, and high tear strength, a process for producing the film and an intended use thereof.

BACKGROUND ART

From the past, porous polyolefin films having a number of small holes resulting from an inorganic filler are produced by stretching an unstretched film of polyolefin incorporated with the inorganic filler.

These porous polyolefin films are, however, opaque throughout the films and poor in see-through property due to low light transmission so that it is hard to confirm the color and the state of an article existing on the opposite surface of the film.

In a disposable diaper using the aforesaid porous polyolefin film as back-sheet, for example, the state of excreted urine or excreta could not be visibly confirmed so that a problem arose in delayed time of exchanging for a new diaper.

Accordingly, a device for enhancing light transmission of the film has been made for the application where the see-through property is demanded as in back-sheet for disposable diapers.

For example, there is proposed a porous polyolefin film provided with partial see-through property by subjecting a porous polyolefin film to an embossing treatment and fusing the resin in microporous portions to collapse voids (Japanese Laid-open Patent Appln. No. Hei. 5-168660), etc. In such porous films, mechanically formed portions higher in light transmission exist locally, through which portions it is at any rate possible to observe the opposite surface.

TECHNICAL SUBJECT OF THE INVENTION

However, porous polyolefin films of a non-homogeneous series obtained according to the embossing method, which contain non-porous portions or low porous portions and porous portions in mixed state, are poor in see-through property in the porous portions so that degradation of the moisture permeability is obliged to take place for sufficiently enhancing the see-through property of the whole film. For this reason, the light transmission of a porous polyolefin film obtained according to embossing was generally at most about 60%.

A porous polyolefin film possessing coarse embossed portions varies the ratio of the non-(or lower-)porous portions to the porous portions, thus forming difference in the physical properties of the film, such as moisture-permeability.

As a countermeasure for the aforementioned, a means for extremely minimizing the interval of embossed portions is thinkable in the embossing treatment. As a result of see-through property in the embossed portions being equalized by the adjacent porous portions by minimizing the intervals of the embossed portions, however, there may be the case wherein the see-through property is degraded.

In case the porous polyolefin film is used as a back-sheet or the like, on the other hand, a high degree of tear strength is also required lest the sheet should be broken on the use. However, the porous polyolefin film wherein the non-homogeneous portions having been formed by the aforesaid embossing still leaves room for improvement in this point.

Accordingly, it is an object of the present invention to provide a porous polyolefin film possessing sufficient moisture-permeability, high light transmission and high tear strength in spite of being uniformly made porous throughout the film.

DISCLOSURE OF THE INVENTION

As a result of extensive research for solving such problem, the present inventors has succeeded in development of a porous polyolefin film capable of achieving all of the aforesaid objects by producing a porous polyolefin film with a resin composition incorporated with an inorganic filler together with a wax of polyolefin series.

In accordance with the present invention, there is provided a porous polyolefin film which comprises a polyolefin containing an inorganic filler and a wax of polyolefin series, the film being provided with micropores originated from the inorganic filler, a water vapor transmission rate of at least 1000 $g/m^2 \cdot 24$ hours, a light transmission of at least 65%, and a tear strength of at least 0.6 N, and the film having a uniform moisture-permeability throughout.

In accordance with the present invention, there is also provided, as a preferable process for producing the porous polyolefin film, a process for producing a porous polyolefin film which comprises stretching an unstretched polyolefin film having a resin composition of 100 parts by weight of polyolefin, 50–150 parts by weight of an inorganic filler having a 50% median diameter of at least 2 $\mu m$ but less than 7 $\mu m$ measured according to the light-scattering method, and 2–20 parts by weight of a wax of polyolefin series in at least uniaxial direction at an area magnification of 1.1–1.5 times, In accordance with the present invention, there is further provided a composite porous polyolefin film composed of the porous polyolefin film and a non-woven fabric of polyolefin series as well as a back-sheet for disposable diapers which comprises the above porous polyolefin film or the above composite porous polyolefin film.

BEST MODE FOR CARRYING OUT THE INVENTION

The porous polyolefin film of the present invention comprises polyolefin containing an inorganic filler and a wax of polyolefin series.

As a material for the inorganic filler, any of the known inorganic fillers used heretofore for producing porous polyolefin film may be employed without any limitation. Mentioned, for example, are calcium carbonate, gypsum, calcium sulfite, calcium phosphate, magnesium carbonate, silicic acid hydrate, silicic anhydride, soda lime, sodium chloride, barium sulfate, talc, clay, various kinds of cement, volcanic ash, shirasu, titanium oxide, iron oxides, carbon black, various kinds of metal powder, and organic metal salts containing inorganic substances or mainly inorganic substances. Among these exemplified, calcium carbonate is especially preferred.

As described in detail hereinafter, the inorganic filler functions synergestically with the wax to increase light transmission due to micropores based thereon and to improve see-through property so that the filler having a 50% median diameter measured according to the light-scattering method (referred to hereinafter simply as "the median diameter") of at least 2 μm but less than 7 μm, especially 2.5–5.5 μm is preferably used.

No limitation exists in the polyolefin in the porous polyolefin film of the present invention. However, illustrative of the representative one are homopolymers of α-olefins such as polyethylene, polypropylene, polybutene-1, and poly-(methylpentene), copolymers of α-olefins with other copolymerizable monomers, and a mixture of these polymers. No particular limitation exists in the monomers copolymerizable with the α-olefin and known monomers can be employed, but α-olefins having 2–8 carbon atoms are generally preferable.

Among the aforesaid polyolefins, polyethylene, polypropylene, propylene-ethylene copolymer, and a linear low density polyethylene produced according to the intermediate or low pressure method are preferable. In particular, a linear low density polyethylene preferable as it affords good flexibility.

The aforesaid polyolefin constitutes a skeleton of the porous polyolefin film and so preferably has a melt flow rate of 1–30 g/10 minutes, preferably 0.5–10 g/10 minutes for fully exhibiting the strength such as tear strength mentioned hereinafter.

In the present invention, the wax of polyolefin series is important, as it functions synergestically together with the inorganic filler added to imparts a high degree of light transmission to the porous polyolefin film. Further, the wax of polyolefin series is preferable in the point of workability such as extrusion or of non-odor.

The wax of polyolefin is a general term for low molecular weight polyolefins which are solid at normal temperature. In more detail, low molecular weight polyethylene and low molecular weight polypropylene are representative. In case of the low molecular weight polyethylene (polyethylene wax), its number average molecular weight is preferably 900–10000, in particular 1500–6000. In case of the low molecular weight polypropylene (polypropylene wax), its number average molecular weight is preferably 1000–15000, in particular 3000–10000 As these waxes, polarized waxes such as an oxide type wax or a maleic acid-modified wax can be used without any problem.

Among these waxes of polyolefin, a low molecular weight polyethylene capable of enhancing see-through property is particularly preferred.

The porous polyolefin film of the present invention is characterized by containing the inorganic filler and the wax of polyolefin series.

A conventional porous polyolefin film is obtained by stretching an unstretched film of polyolefin containing the above inorganic filler alone. The film thus obtained is uniform and possesses a high moisture permeability but is less than 50% in light transmission and is extremely poor in see-through property.

The film becomes desirably thin for enhancing light transmission. In order to attain extremely outstanding light transmission of at least 65% specified in the present invention, however, the thickness of the film has to be not more than 10 μm. In this case, tear strength of the film is considerably reduced to about 0.2 N.

Contrary to this, the porous polyolefin film of the present invention employing the wax of polyolefin series together with the inorganic filler can achieve extremely high degree of moisture permeability, light transmission and tear strength and need not be subjected separately to an embossing treatment so that uniform moisture permeability can be imparted to all over the film.

Thus, the porous polyolefin film of the present invention possesses a water vapor transmission rate of at least 1000 $g/m^2 \cdot 24$ hrs, in particular 1100–2000 $g/m^2 \cdot 24$ hrs.

In the present invention, the moisture permeability is shown as an average value of the individual measured values obtained by sampling 5 circular portions each having a diameter of 40 mm arbitrarily from the film, measuring for each circular portion a water vapor permeated amount in the period of 24 hours under the condition that a temperature is 40° C. and a humidity is 60% and converting the measured amount into a moisture permeability in terms of $m^2$.

The porous polyolefin film of the present invention possessing such an excellent moisture permeability exhibits a high function in prevention of a stuffy condition when used as a back-sheet for disposable diapers.

Further, the porous film of the present invention possessing uniform moisture permeability throughout the film stably exhibits the aforesaid function in any of the portions of the film.

By the way, scattering of the aforesaid uniform moisture permeability in the porous polyolefin film of the present invention is within the range of ±20%, in particular ±15%. The scattering of the moisture permeability is shown in terms of percentage by sampling 5 circular portions of 40 mm in diameter from the film, measuring moisture permeability of the individual portions and dividing the individual measured values by an average value thereof.

In contrast, a porous polyolefin film obtained by subjecting the porous film to embossing treatment or subjecting the film to partial stretching to enhance light transmission contains non-(or lower-)porous portions and porous portions in mixed state so that the proportion of both portions is different according to the sampled portions to make it difficult to obtain such uniform moisture permeability.

In case the non-(or lower-)porous portions and the porous portions are formed in a minimized unit, scattering of the moisture permeability will become smaller. In this case, however, the enhancing effect of light transmission will be deteriorated to make it difficult to obtain a high degree of light transmission as in the present invention.

As described above, the porous film of the present invention possesses an outstanding see-through property shown by light transmission of at least 65%, in particular 70–80%, while maintaining uniform and extremely high moisture permeability.

Thus, high see-through property is very useful in confirming the internal state of the back-sheet for disposable diapers.

The porous polyolefin film of the present invention is significant in strength; its tear strength is at least 0.6 N, in particular at least 1 N, so that stable characteristics can be exhibited in handling of the film alone or use as the back-sheet. In the use of the back-sheet for disposal diapers, for example, difficulty in tear of the film is further enhanced even in case immoderate force is applied at the time of wearing or detaching.

In the porous polyolefin film of the present invention, no particular limitation exists in thickness of the film. In relation with the light transmission and tear strength, etc., however, the thickness is preferably 20–50 μm, more preferably 20–40 μm. Further, the porous polyolefin film of the present invention usually has a hydraulic pressure resistance of at least 15 KPa, preferably 25–200 KPa.

No particular limitation exists in the process for producing the porous polyolefin film of the present invention. Illustrative of the representative process for production is a process wherein unstretched polypolefin film having a resin composition of 100 parts by weight of polyolefin, 50–150 parts by weight of an organic filler having a median diameter of at least 2 μm but less than 7 μm, and 2–20 parts by weight of a wax of polyolefin series is stretched at least in uniaxial direction at an area magnification of 1.1–1.5 times.

In the process for producing the porous polyolefin film of the present invention, it is preferred to use an inorganic filler having a median diameter of at least 2 μm but less than 7 μm, preferably at least 2.5–5.5 μm.

In case the median diameter is not more than 2 μm, the light transmission of the resultant porous polyolefin film tends to deteriorate even if the wax is jointly used. In case the median diameter is at least 7 μm, the light transmission is enhanced but the film tends to be torn and the tear strength tends to deteriorate due to increase in granular diameter of the inorganic filler.

Considering the molding property of the film, the inorganic filler preferably has such a granule distribution that at least 95% by weight, preferably at least 99% by weight of the whole filler has preferably a granular diameter of 0.01255–25 μm, more preferably 0.05–20 μm.

In the process for producing the porous polyolefin film of the present invention, the inorganic filler is 50–150 parts by weight, preferably 80–120 parts by weight for 100 parts by weight of the polyolefin. If the proportion of the inorganic filler is less than 50 parts by weight, the formation of continuously communicated holes will become difficult to make moisture permeability poor. If the proportion of the inorganic filler is more that 150 parts by weight, a number of very fine holes will be generated to make it difficult to obtain a porous film having the aforesaid high degree of light transmission.

The proportion of the wax of polyolefin series is 2–20 parts by weight per 100 parts by weight of the polyolefin resin. Especially, in case the wax is 3–10 parts by weight, the characteristics of the porous polyolefin film can sufficiently be exhibited.

Concerning the effect of the wax of polyolefin added, it is presumed that relatively transparent unstretched portions or weakly stretched portions and whitened stretched portions of a micron order are shown in minutely mixed state in the film after stretching, unlike irregular stretching due to the conventional machine, so that transparency and moisture permeability are exhibited throughout the film.

Accordingly, if the amount of the wax added to the polyolefin is smaller than 2 parts by weight, the film will be stretched evenly, thus resulting in promotion of whitening throughout the film so that the resultant porous polyolefin film tends to become poor in light transmission. On the other hand, if the amount of the wax added is more than 20 parts by weight, not only unevenness in whitening will tend to become coarse adversely, but also molding stability will tend to become poor.

In the present invention, the polyolefin may conveniently be incorporated with other thermoplastic resins, pigments, stabilizers, surfactants, plasticizers, oils, and the like additives at need so far as the object of the present invention be not damaged.

No special limitation exists in the method of mixing the polyolefin with the inorganic filler, and any of the known methods can be adopted. It is general to mix them, for example, with a super mixer, Henshell mixer or the like and to pelletize the mixture with a biaxial extruder of high kneading type or the like.

The porous polyolefin film of the present invention can be obtained by stretching an unstretched film having a composition of the polyolefin, the inorganic filler and the wax of polyolefin series in at least uniaxial direction.

The aforesaid stretching is preferably biaxial stretching. Representative is a method wherein the unstretched film is molded, for example, by using a T-die or a circular-die, uniaxially stretched according to a roll-stretching method and then successively biaxially stretched by way of Tenter stretching machine, an air-inflation method, a mandrel stretching method, etc.

Among these methods, a method wherein the unstretched film is tubularly molded by way of an air-inflation method, the film is stretched in a first uniaxial direction (lengthwise) by way of a roll stretching machine and then the film is stretched in a second uniaxial direction (lateral) by way of a mandrel stretching method is especially preferably adopted in the point that this method is better in balance of film orientation at the time of extrusion of the film and is excellent in tear strength after the biaxial stretching, as compared with the T-die biaxial stretching method.

A stretching ratio in the aforesaid stretching is desirably as small as possible for obtaining a film higher in light transmission so far as the moisture permeation be not damaged. In usual, a range of 1.1–1.5 times, preferably 1.2–1.4 times in terms of area magnification is preferable to obtain a porous polyolefin film having a high degree of light transmission. In case the area magnification is smaller than 1.1 times, the formation of continuously communicated holes is not sufficient to make it difficult to obtain a high moisture permeability. In case the area magnification is larger than 1.5 times, a number of voids are formed so that relatively transparent portions in the film is decreased to make it difficult to obtain sufficient light transmission.

The stretching is preferably carried out a temperature lower than the melting point of the resin component, above all, at a temperature 10° C. lower than the melting point. Subsequent to the stretching step, a thermal treatment or a surface treatment such as corona discharge, etc. may be carried out.

As the porous polyolefin film of the present invention is excellent in light transmission and moisture permeability, the film can be laminated with a non-woven fabric of polyolefin series to form a composite porous polyolefin film excellent in light transmission and moisture permeation. Accordingly, this composite porous polyolefin film can also be used for sanitary supplies such as back-sheet for disposable diapers as in the porous polyolefin film of the present invention and for other materials in medical and constructive fields.

Especially in case of using the film as a back-sheet for disposable diapers, the film exhibits superior properties such that the internal state can visibly be confirmed, both leak-preventing property and moisture permeation are good, and the film shows textile-like structure.

For using the film as back-sheet for disposable diapers exhibiting high function for preventing stuffy state and for being useful to visibly confirming the internal state, the film is preferably in the form of a composite porous polyolefin film having a light transmission of at least 65% and a water vapor transmission rate of at least 1000 $g/m^2 \cdot 24$ hours.

In order to regulate the light transmission of the composite porous polyolefin film to at least 65%, it is preferred that the starting porous polyolefin film of the present invention has a light transmission of at least 70%. In order to regulate the moisture permeability of the composite porous polyolefin film to at least 1000 g/m$^2$·24 hours, it is preferred that the starting porous polyolefin film of the present invention has a water vapor transmission rate of at least 1100 g/m$^2$·24 hours.

A material or structure for the known non-woven fabric of polyolefin series can be used without any special limitation for the material and structure of non-woven fabric of polyolefin series to be laminated with the porous polyolefin film of the present invention for making a composite porous polyolefin film.

As the material, for example, polyethylene, polypropylene, ethylene-propylene copolymer, etc. are preferable, and these polyolefins may be used singly or as composition.

As a structure of fibers constituting the non-woven fabric of polyolefin series, sole fibers of the aforesaid polyolefin, a sheath-core structure where the kinds of the resin are varied in the portions of sheath and core, and a side-by-side structure, etc. can be used without any limitation. In addition, a structure constituted according to a known method such as the spun-bond method, the dry method and a special melt-blow method is adopted without any special limitation.

The aforesaid non-woven fabric of polyolefin series is preferably has a light transmission of at least 85% in order to raise a light transmission of a composite porous polyolefin film, which has been made by laminating the porous polyolefin film with the non-woven fabric of polyolefin series, to at least 65%.

Mentioned as a preferable embodiment for attaining the light transmission of the non-woven fabric of polyolefin series is mentioned an embodiment wherein the basis weight of the non-woven fabric of polyolefin series is defined as not more than 25 g/m$^2$, preferably not more than 20 g/m$^2$. If the basis weight exceeds 25 g/m$^2$, a space clogged by fibers is increased to make it difficult to attain the above light transmission. On the other hand, if the basis weight is at least 10 g/m$^2$, preferably at least 12 g/m$^2$, it is preferable to impart cotton-like feeling to the composite porous polyolefin film.

It is preferable that the fiber diameter of the non-woven fabric of polyolefin series is 10–50 $\mu$m, preferably 15–30 $\mu$m. In case the fiber diameter is less than 10 $\mu$m, the light transmission will tend to deteriorate. If the value is larger than 50 $\mu$m, the resultant composite porous polyolefin film will be damaged in flexibility.

A known lamination method wherein the porous polyolefin film is not damaged in air-permeability is preferably adopted for a method for laminating the porous polyolefin film with the non-woven fabric of polyolefin series for constituting the composite porous polyolefin film. Namely, lamination for making composite materials can be effected according to the method for dry lamination and hot melt lamination wherein a binder is used or the method for thermal lamination wherein no binder is used.

For these binding methods, a method wherein a binder is sprayed or applied spirally at random and then binding is effected as in hot melt binding can preferably be used in addition to a regular intermittent binding such as a dot-like, lattice-like or linear binding.

As a binder for binding the non-woven fabric of polyolefin series with the porous polyolefin film, a binder of an urethane-type, a rubber-type, an epoxy-type or a vinyl acetate-type is used for the dry lamination method, while a binder of an olefin-type, an ethylene-vinyl acetate-type and a synthetic rubber type is used for the hot melt lamination method. In the thermal lamination method, the melting point of a resin of the non-woven fabric is preferably similar to or lower than the melting point of a resin constituting the porous polyolefin film. For example, the sheath fiber constituting the non-woven fabric is a low density polyethylene while the core fiber is polypropylene, or a composite fiber of a low density polyethylene and polypropylene in the side-by-side form is applied to the porous polyolefin film constituting a low density polyethylene.

In consideration of the required softness, moisture permeability and light transmission in respect of binding, it is preferable that the binding area is as small as possible. On the other hand, however, at least a certain constant area is necessary for binding in consideration of the total tensile strength and binding strength, so that it is general that fusing and binding is effected within a area range of about 5–30%.

EXAMPLE

Examples and Comparative Examples are given hereinafter, but the present invention is not limited by these Examples.

The measurement of physical properties listed in Examples and Comparative Examples is carried out in the following methods:

1) Median diameter of the inorganic filler:
   The measurement was carried out with a measuring device using the light scattering method manufactured by Shimazu Seisakusho, SALD-2000.

2) Light transmission:
   Transparency was measured by using a Haze computer HGM-2DP manufactured by Suga Shikenki in accordance with JIS K7105 and shown as light transmission.

3) Water vapor transmission rate (Moisture permeability):
   In arbitrary 5 positions of the porous film, a circular portion of 40 mm in diameter were sampled and each circular portion was measured for the amount of water vapor permeation under the condition of a temperature 40° C. and a relative humidity of 60% for 24 hour in accordance with ASTM E-96. The measured values were converted into a water vapor transmission rate in terms of m$^2$. An average value of the measured values in 5 positions is shown as the water vapor transmission rate. Scattering of the values is also shown according to the above calculation method.

4) Hydraulic pressure resistance:
   The measurement was carried out in accordance with JIS L 1092 B.

5) Tear Strength:
   The tear strength of the film in MD direction was measured in accordance with JIS K 7128 A.

Examples 1–13

A composition obtained by incorporating 100 parts by weight of a linear low density polyethylene [density: 0.92 g/cm$^3$, melt index (MI): 2.0 g/10 min. manufactured by Idemitsu Sekiyu Kagaku KK, trade name: Idemitsu LL0234CL] with a heavy calcium carbonate shown in Table 1 and a wax of polyolefin series shown in Table 2 (density: 0.92 g/cm$^3$, viscosity: 4300 mPa·s, trade name: Sun wax 161PP; density: 0.96 g/cm$^3$, viscosity: 650 mPa·s, trade name: Sun wax LEL400P(EX); and density: 0.89/cm$^3$, viscosity: 4000 mPa·s, trade name: Viscole 330P; each manufactured by Sanyo Kasei Kogyo KK] in a proportion shown in Table 3 was molten in a biaxial kneading extruder at a cylinder temperature of 200° C. to obtain kneaded product in pellet form.

Using an inflation extruder, this pellet was molded into a tubular film of 400 mm in diameter at a cylinder temperature of 175° C., a die temperature of 170° C. and a take-up speed of 10 m/min., stretched in longitudinal direction by the aid of a roll stretcher at normal temperature, and successively stretched in lateral direction by the aid of a mandrel stretcher at a temperature of 80° C. whereby each porous film was obtained.

By the way, the area magnification is shown in Table 3. A thickness of each resultant porous polyolefin film is shown in Table 4.

Various physical properties of the porous polyolefin films thus obtained were measured and shown in Table 4.

Comparative Example 1 and 2

In the foregoing Examples, various compositions shown in Table 3 without using the wax were used to obtain porous polyolefin films in accordance with the above Examples. A thickness of each resultant porous polyolefin film is shown in Table 4.

Various physical properties of the porous polyolefin films thus obtained were measured and shown in Table 4.

Referential Example 1

Physical properties of a commercially available porous polyolefin film (thickness: 25 μm) were measured in the same manner as illustrated in Examples, the film having been obtained according to the stretching method from a resin containing as predominant components a linear low density polyethylene filled with calcium carbonate having a median diameter of 1.2 μm as the inorganic filler.

A result of the measurement is shown also in Table 4.

TABLE 1

| | 50% | | Distribution of granularity (Wt %) | | |
|---|---|---|---|---|---|
| Grade name | Median diameter | Maximum diameter | 0.05–2 μm | 2–20 μm | Over 20 μm |
| A BSK-5D (4.8 μm) | 4.8 | 25 | 31.0 | 68.9 | 0.1 |
| B CSK-5T (2.8 μm) | 2.8 | 20 | 36.5 | 63.5 | 0 |

*Calcium carbonate in Table 1 is all manufactured by Dowa Calfine KK.

TABLE 2

| Wax of polyolefin series | | | | |
|---|---|---|---|---|
| Trade name | Material | Density | Viscosity (mPa·s) | Number average molecular weight |
| I Sun wax 161-P*1 | Polyethylene series | 0.92 (20° C.) | 4300 (140° C.) | 5000 |
| II Sun wax LEL-400P (EX)*2 | Polyethylene series | 0.96 (20° C.) | 4300 (140° C.) | 4000 |
| III Viscol 330-P*3 | Polypropylene series | 0.89 (20° C.) | 4300 (160° C.) | 15000 |

*1–*3 All are manufactured by Sanyo Kasei Kogyo KK

TABLE 3

| | Inorganic filler | | Proportion of Wax of PO series per 100 parts | Stretching |
|---|---|---|---|---|
| | Kind | Amount filled (Parts by wt.) | by weight of resin (Parts by weight) | ratio (Area) |
| Example 1 | A | 85 | 6 (Wax I) | 1.2 |
| Example 2 | B | 85 | 6 (Wax I) | 1.2 |
| Example 3 | B | 66 | 6 (Wax I) | 1.3 |
| Example 4 | B | 120 | 8 (Wax I) | 1.15 |
| Example 5 | B | 85 | 6 (Wax I) | 1.3 |
| Example 6 | B | 85 | 10 (Wax I) | 1.25 |
| Example 7 | B | 85 | 20 (Wax I) | 1.25 |
| Example 8 | B | 85 | 6 (Wax I) | 1.15 |
| Example 9 | B | 85 | 6 (Wax I) | 1.4 |
| Example 10 | B | 85 | 6 (Wax I) | 1.15 |
| Example 11 | B | 85 | 3 (Wax II) | 1.3 |
| Example 12 | B | 110 | 6 (Wax II) | 1.2 |
| Example 13 | B | 85 | 6 (Wax III) | 1.25 |
| Comparative Example 1 | A | 85 | 0 | 1.2 |
| Comparative Example 2 | B | 85 | 0 | 1.2 |

TABLE 4

| | Physical properties | | | | |
|---|---|---|---|---|---|
| | Thickness (μm) | Light transmission (%) | Water vapor transmission rate | | Tear strength (N) |
| | | | (g/m²·24 hours) | S*2 | H.P.R.*1 (kPa) |
| Example 1 | 25 | 70 | 1200 | ±20% | 150 | 1.2 |
| Example 2 | 22 | 71 | 1500 | ±15% | 180 | 1.4 |
| Example 3 | 21 | 70 | 1300 | ±15% | 160 | 1.2 |
| Example 4 | 25 | 70 | 1500 | ±15% | 200 | 1.1 |
| Example 5 | 22 | 70 | 1550 | ±15% | 170 | 1.5 |
| Example 6 | 24 | 70 | 1600 | ±15% | 150 | 1.6 |
| Example 7 | 28 | 69 | 1650 | ±20% | 130 | 1.3 |
| Example 8 | 25 | 70 | 1300 | ±15% | 180 | 1.5 |
| Example 9 | 25 | 66 | 1700 | ±20% | 160 | 1.3 |
| Example 10 | 45 | 68 | 1000 | ±20% | 200 | 2.0 |
| Example 11 | 27 | 70 | 1800 | ±15% | 140 | 1.7 |
| Example 12 | 27 | 72 | 1500 | ±15% | 170 | 1.4 |
| Example 13 | 22 | 67 | 1200 | ±20% | 140 | 1.3 |
| Comparative Example 1 | 26 | 66 | 600 | ±20% | 150 | 1.4 |
| Comparative Example 2 | 23 | 63 | 1000 | ±20% | 130 | 1.4 |
| Referential Example | 20 | 50 | 980 | ±20% | 130 | 0.3 |

Remarks:
*1H.P.R. means Hydraulic Pressure Resistance.
*2S means scattering (from an average value).

Example 14

In the same proportion and stretching ratio as illustrated in Example 12, a porous polyolefin film was obtained in the same manner as in the foregoing Examples. This porous polyolefin film had a light transmission of 75%, a moisture permeability of 1500 g/m²·24 hours, a scattering of the water vapor transmission rate of ±15%, a hydraulic pressure resistance of 120 kPa, and a tear strength of 1.2 N. Next, a non-woven fabric of polypropylene having a basis weight of 15 g/m² and a of 15 g/m² and a light transmission of 90.5% and the porous polyolefin film were sprayed with a hot melt binder of EVA series in an applying amount of 2 g/m² and bound to obtain a composite porous polyolefin film having a textile feeling complexed with the non-woven fabric. The resultant composite porous polyolefin film had a light transmission of 67%, a moisture permeation of 1400 g/m²·24 hrs and a hydraulic pressure resistance of 120 kPa.

The aforesaid composite porous polyolefin film shows a high degree of light transmission even in combination with the non-woven fabric and suitable, for example, as a back-sheet for diapers of textile feeling externally see-through.

Industrial Applicability

As is understood from the foregoing explanation, the porous polyolefin film of the present invention having a uniform moisture permeability exhibits extremely high moisture permeability and light transmission in combination without being subjected to an embossing treatment, and is a film having a sufficiently high tear strength.

Even in case the film is laminated with a non-woven fabric of polyolefin series to form a composite porous polyolefin film, the resultant film excels in moisture permeability and light transmission and has a textile touch and feeling.

Thus, in case of using the porous polyolefin film as a back-sheet for disposable diapers, it shows good wear feeling due to high moisture permeability. Moreover, the film has the most important properties in combination; good in see-through property of the contents and strong against tear at the time of wearing and detaching, thus showing extremely high usefulness.

The porous polyolefin film of the present invention is not limited to the use for the back-sheet for diapers but is used for a variety of applications utilizing the aforesaid characteristic properties, for example, constructive goods, medical or sanitary goods other than diapers, packaging materials necessitating air permeability, etc.

What is claimed is:

1. A porous polyolefin film which comprises a polyolefin containing an inorganic filler and a wax of polypropylene, the film being provided with micropores originated from the inorganic filler, a water vapor transmission rate of at least 1000 g/m²·24 hours, a light transmission of at least 65%, and a tear strength of at least 0.6 N, and the film having a uniform moisture permeability throughout.

2. A porous polyolefin film according to claim 1, wherein a resin composition constituting the film is comprised of 100 parts by weight of the polyolefin, 50–150 parts by weight of the inorganic filler having a 50% median diameter of at least 2 μm but less than 7 μm measured according to the light scattering method, and 2–20 parts by weight of the wax of polypropylene.

3. A porous polyolefin film according to claim 1 or 2, wherein the polyolefin contains a linear low density polyethylene as a predominant component.

4. A porous polyuolefin film according to claim 1 or 2, wherein the wax of polyolefin series is a low molecular weight of polypropylene.

5. A porous polyolefin film according to claim 1, wherein the film is a biaxially stretched film.

6. A process for producing a porous polyolefin film which comprises stretching an unstretched polyolefin film having a resin composition of 100 parts by weight of polyolefin, 50–150 parts by weight of an inorganic filler having a 50% median diameter of at least 2 μm but less than 7 μm measured according to the light-scattering method, and 2–20 parts by weight of a wax of polypropylene in at least uniaxial direction at an area magnification of 1.1–1.5 times.

7. A process for producing a porous polyolefin film according to claim 6, wherein the porous polyolefin film has a water vapor transmission rate of at least 1000 g/m²·24 hours, a light transmission of at least 65%, and a tear strength of at least 0.6 N and wherein the film has a uniform moisture permeability throughout.

8. A composite porous polyolefin film which is a laminate comprising the porous polyolefin film as set forth in claim 1 and a non-woven fabric of polyolefin series.

9. A composite porous polyolefin film according to claim 8, wherein the film has a light transmission of at least 6% and a water vapor transmission rate of at least 1000 g/m²·24 hrs.

10. A back-sheet for disposable diapers which comprises the porous polyolefin film as set forth in claim 1.

11. A back-sheet for disposable diapers which comprises the porous polyolefin film as set forth in claim 8 or 9.

* * * * *